United States Patent [19]

Stewart et al.

[11] Patent Number: 4,543,191

[45] Date of Patent: Sep. 24, 1985

[54] BS&W IN CRUDE OIL STREAMS

[75] Inventors: Thomas L. Stewart, Houston; Florian C. Demny, Pasadena, both of Tex.

[73] Assignee: Shell Oil Company, Houston, Tex.

[21] Appl. No.: 291,599

[22] Filed: Aug. 10, 1981

[51] Int. Cl.[4] ............................................ G01N 15/04
[52] U.S. Cl. .................................. 210/746; 73/61 R; 134/22.11; 134/166 C
[58] Field of Search ............... 210/636, 742, 746, 773, 210/774, 781; 134/5, 22.1, 22.11, 23, 40, 166 C; 73/61 R, 61.1 R

[56]  References Cited
U.S. PATENT DOCUMENTS

| 2,117,648 | 5/1938 | Bottorf ................................ 134/24 |
| 2,415,729 | 2/1947 | Dana .................................... 134/5 |
| 3,319,710 | 5/1967 | Heeren et al. ................... 134/22.11 |
| 3,546,926 | 12/1970 | Dunavent, Jr. et al. ........... 73/61.1 |
| 4,184,932 | 1/1980 | Stewart ............................. 210/781 |
| 4,225,362 | 9/1980 | Sentell .............................. 134/24 |

Primary Examiner—John Adee

[57] ABSTRACT

Capacitance cells comprising concentric tubes are maintained clean of sediment in the space between the inner and outer tubes where capacitance is measured by (1) suspending fibrous strands in the fluid flow outside the inner tube and/or (2) partially plugging the inner tube to increase flow outside the inner tube.

10 Claims, 2 Drawing Figures

BS&W IN CRUDE OIL STREAMS

BACKGROUND OF THE INVENTION

A device for measurement of basic sediment and water (BS&W) in a predominantly non-aqueous stream (e.g. pipeline crude oil) is disclosed in U.S. Pat. No. 4,184,952. This device is an improvement on capacitance type instruments of the art which are dependent upon the extent to which the intrinsic dielectric constant of the subject fluid varies with time. The gravity and physical composition of crude oil are two factors which determine its intrinsic dielectric constant. If one or both of these properties should vary, instruments measure the accompanying change in the dielectric constant as percent BS&W. This yields an inaccurate measurement of BS&W because instruments must be initially set to read zero BS&W as the intrinsic dielectric constant of the fluid. The capacitance type instruments of the prior art have no means for automatically correcting the zero BS&W setting to compensate for periodic variations in the oil properties mentioned. By comparison, the device of U.S. Pat. No. 4,184,952 provides for automatic compensation of BS&W measurements by producing a clean, dry sample of the line fluid for measurements of its intrinsic dielectric constant. In this way, the true BS&W content of the fluid is measured by finding the difference between the dielectric constants of the wet and dry streams.

Even though the improvement over the art represented by the invention of U.S. Pat. No. 4,184,952 is substantial, it now has been discovered that other improvements can be made which even further improve the efficiency and accuracy of this invention. Thus, variance in flow between between the cells utilized for measuring capacitance in the wet and dry streams of the BS&W recorder can cause loss of accuracy of readings. For example, with the device disclosed in U.S. Pat. No. 4,184,952, the flow through a cell utilized to measure capacitance of a wet stream would be about 5 to 100 times that through a cell utilized to measure capacitance of a dry stream. This cannot be avoided because isokinetic sampling and sampling tube diameter require relatively high wet stream flow, while dry stream output from the centrifuge of the apparatus of U.S. Pat. No. 4,184,952 is relatively low. The low velocity in the dry cell allows (1) accumulation of residue and causes (2) a time delay of several minutes in the dry cell perception of the arrival of a new batch of oil. Since the time delay is fairly constant, it can be calculated out by computer or microprocessor, but elimination of time delay and increasing velocity in the dry cell are both desirable goals.

It would initially appear that an improvement to the BS&W instrument would be to reduce the size of the dry cell so that the velocity of the oil through it would approximately equal flow through the wet cell. However, having cells of two different sizes would introduce complex calibration problems. Thus, it is desirable to have both the cells identical.

As noted, one problem caused by low velocity in the dry cell is the accumulation of residue such as wax. Such residue may result not only from low velocity but also from temperature variations as mentioned in applicants' co-pending application Ser. No. 291597 filed Aug. 10, 1981. Thus, the cell consists of two coaxial tubes electrically insulated from each other wherein the annular space between the tubes constitutes an electrical capacitor whose value depends upon the material in the annular space. Residue usually tends to cause an error in the direction of wetness. Thus, the dry cell indicates less dry than it should compared to the wet cell where flow is more rapid and residue does not tend to accumulate.

Accordingly, the present invention provides solutions to overcoming the above noted problem wherein relatively slow flow in the wet cell allows accumulation of residue.

SUMMARY OF THE INVENTION

The present invention provides a process and apparatus for reducing the inequality of flow velocity within at least two dimensionally similar BS&W monitors, both of which have capacitance cells of at least two concentric tubes through which a liquid to be monitored is flowed, one of said monitors normally having a substantially greater volumeric flow than the other of said monitors, comprising partially blocking the inner tube of the lesser flow monitor to increase the flow between the inner and outer tubes and to reduce the inequality with flow between the inner and outer tubes of the greater flow monitor.

The present invention further includes a process and apparatus for continuously cleaning a BS&W monitor which has a capacitance cell of at least two concentric tubes through which a liquid to be monitored is flowed, comprising suspending one or more flexible strands in the current flow within the concentric tubes, whereby the strands function to maintain the tube walls clean. Preferably, the strands are fibrous and are suspended from non-conductive spacers separating the tubes.

DESCRIPTION OF PREFERRED EMBODIMENTS

Figure 1:
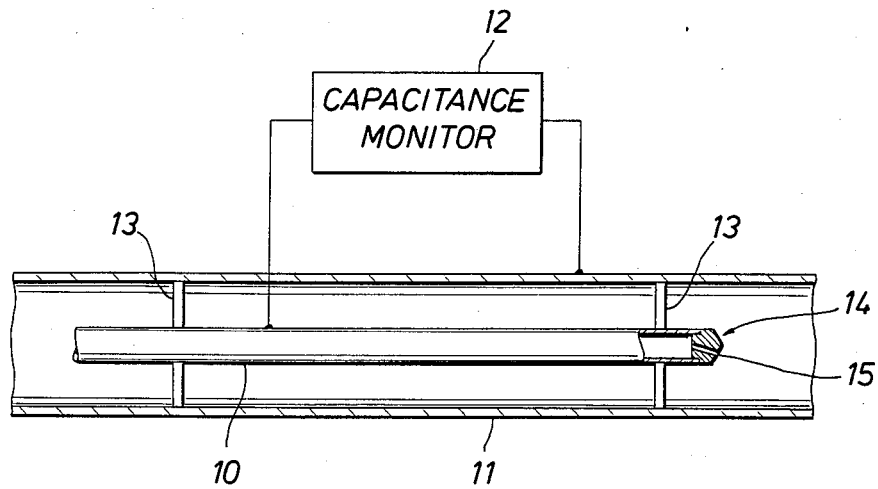
FIG. 1 schematically discloses the capacitance measurement cell of the present invention with means for selectively increasing the flow in part of the cell.

In FIG. 1 an oil and water probe assembly cross section of a typical capacitance type monitor is shown. Reference may be had to U.S. Pat. Nos. 3,189,180; 3,546,926 and 3,006,189 for other capacitance-type monitors. Generally, the capacitance cell monitor includes two coaxial tubes comprising an inner tube 10 and an outer tube 11. The fluid to be monitored passes through the inner tube and between the inner tube and the outer tube. The capacitance is detected between the inner and outer tubes by a variable capacitance and sensor 12. The two coaxial tubes are electrically insulated from each other by an annular spacer 13 which is nonconductive. In accordance with the present invention, the inner tube 10 is partially blocked by a plug 17 having a hole 15 which allows some flow through the tube. Generally, the hole 15 is arranged at an angle to the plug so that flow follows a swirling movement inside the inner tube, thereby facilitating keeping it reasonably clean. Such partial plugging of the inner tube causes more of the flow to pass between the inner and outer tubes, thereby sweeping the space between the inner and outer tubes free of residue.

Figure 2:
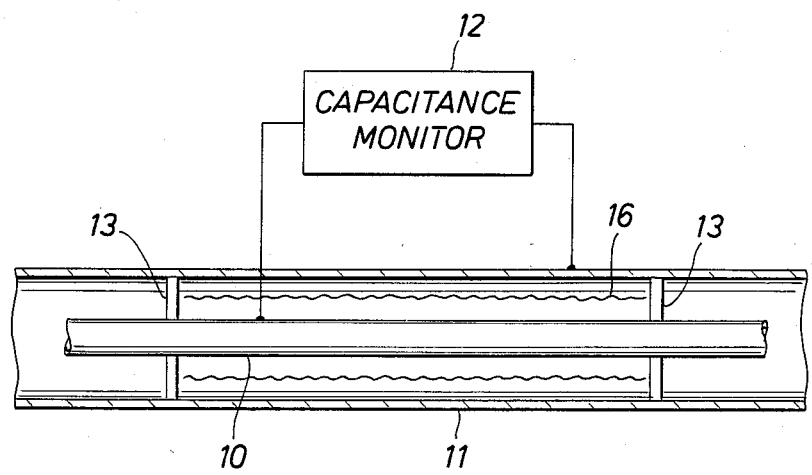
FIG. 2 schematically discloses the capacitance measurement cell of the present invention with means for cleaning the outer tube of the cell.

FIG. 2 of the invention shows another technique for keeping the space between the inner and outer tubes of the capacitance cell clean. The parts of this tube are arranged in the same manner as the parts of the tube of FIG. 1. Strand-like fibers 16 or other flexible materials are arranged to hang in the flow space between the inner and outer tubes. With turbulent flow, the strands or filaments tend to sweep the space clean of any residue which might otherwise collect. Preferably, the strands are suspended from the insulating spacers 13, although it will be apparent that other means may be employed to suspend the strands in the space.

What is claimed is:

1. A process for reducing inequality between flow velocity within at least two dimensionally similar BS&W monitors, both of which have capacitance cells of at least two concentric tubes through which a liquid to be monitored is flowed, one of said monitors normally having a substantially greater volumetric flow than the other of said monitors, comprising, partially blocking the inner tube of the lesser flow monitor to the extent necessary to increase flow between the inner and outer tubes and to reduce inequality with flow between the inner and outer tubes of the greater flow monitor.

2. The process of claim 1 wherein volumetric flow through the greater flow monitor is about 2 to 100 or more times that of the lesser flow monitor.

3. A process for continuously cleaning a BS&W monitor which has a capacitance cell of at least two concentric tubes through which a liquid to be monitored is flowed, comprising suspending one or more fibrous strands longitudinally in the current flow within the concentric tubes, whereby the strands function to clean the walls of the tubes.

4. The process of claim 3 wherein the strands are suspended from nonconductive spacers separating the tubes.

5. The process of claim 3 wherein the liquid is waxy crude oil.

6. Apparatus for reducing inequality between flow velocity within at least two dimensionally similar BS&W monitors, both of which have capacitance cells of at least two concentric tubes through which a liquid to be monitored is flowed, one of said monitors normally having a substantially greater volumetric flow than the other of said monitors, comprising, means for partially blocking the inner tube of the lesser flow monitor to the extent necessary to increase flow between the inner and outer tubes to reduce inequality with flow as between the inner and outer tubes of the greater flow monitor.

7. The apparatus of claim 6 wherein the blocking means is a plug with a centrally located hole.

8. The apparatus of claim 7 wherein the hole is directed to impart a swirling motion to liquid passing through the partially blocked tube.

9. Apparatus for continuously cleaning a BS&W monitor which has a capacitance cell of at least two concentric tubes through which a liquid to be monitored is flowed, comprising, one or more flexible strands suspended longitudinally in the current flow within the concentric tubes.

10. The apparatus of claim 9 wherein the strands are fibrous and are suspended from nonconductive spacers separating the tubes.

* * * * *